US012558180B2

(12) United States Patent
Sitti et al.

(10) Patent No.: US 12,558,180 B2
(45) Date of Patent: Feb. 24, 2026

(54) METHOD FOR CONTROLLING A MOVEMENT OF A MEDICAL DEVICE IN A MAGNETIC FIELD

(71) Applicant: Max-Planck-Gesellschaft zur Förderung der Wissenschaften e.V., Munich (DE)

(72) Inventors: Metin Sitti, Stuttgart (DE); Martin Phelan, Stuttgart (DE)

(73) Assignee: Max-Planck-Gesellschaft zur Förderung der Wissenschaften, e.V., Munich (DE)

( * ) Notice: Subject to any disclaimer, the term of this patent is extended or adjusted under 35 U.S.C. 154(b) by 731 days.

(21) Appl. No.: 17/816,774

(22) Filed: Aug. 2, 2022

(65) Prior Publication Data

US 2024/0041550 A1     Feb. 8, 2024

(51) Int. Cl.
A61B 34/00        (2016.01)
A61B 1/00         (2006.01)
(Continued)

(52) U.S. Cl.
CPC .......... A61B 34/73 (2016.02); A61B 1/00158 (2013.01); A61B 18/1445 (2013.01); *A61B 1/05* (2013.01); *A61B 1/0684* (2013.01); *A61B 1/313* (2013.01); *A61B 2018/00577* (2013.01); *A61B 2018/00982* (2013.01); *A61B 2034/731* (2016.02); *A61B 2090/374* (2016.02); *A61B 2218/002* (2013.01); *A61M 25/0127* (2013.01)

(58) Field of Classification Search
CPC ................ A61B 34/73; A61B 1/00158; A61B 2034/731; A61B 2090/374; A61M 25/0127
See application file for complete search history.

(56) References Cited

U.S. PATENT DOCUMENTS 5,681,260 A * 10/1997 Ueda .................. A61B 1/00082
                                              600/117
6,304,769 B1 * 10/2001 Arenson .................. A61B 5/06
                                              604/528

(Continued)

OTHER PUBLICATIONS

P. Moftakhar et al.: "New-Generation Laser-lithographed Dual-Axis Magnetically Assisted Remote-controlled Endovascular Catheter for Interventional MR Imaging: In Vitro Multiplanar Navigation at 1.5 T and 3 T versus X-ray Fluoroscopy." Radiology: vol. 277: No. 3, pp. 842 to 852, Dec. 2015.

(Continued)

*Primary Examiner* — Anh T Nguyen
*Assistant Examiner* — Shankar Raj Ghimire
(74) *Attorney, Agent, or Firm* — Pearl Cohen Patentanwälte PartGmbB; Michael McCandlish

(57)        ABSTRACT
A method for controlling a movement of a medical device in a magnetic field, the medical device having a set of coils includes determining a torque that needs to be applied onto the medical device such that the medical device carries out the movement, determining a minimum current that needs to be supplied to each coil of the set of coils, respectively, to reach the determined torque by solving an optimization problem, and supplying the determined minimum current to each coil of the set of coils, respectively, such that the medical device carries out the movement.

38 Claims, 9 Drawing Sheets

(51) Int. Cl.

| | |
|---|---|
| *A61B 18/14* | (2006.01) |
| *A61M 25/01* | (2006.01) |
| *A61B 1/05* | (2006.01) |
| *A61B 1/06* | (2006.01) |
| *A61B 1/313* | (2006.01) |
| *A61B 18/00* | (2006.01) |
| *A61B 90/00* | (2016.01) |

(56) References Cited

U.S. PATENT DOCUMENTS

| | | | | |
|---|---|---|---|---|
| 6,504,666 | B1 * | 1/2003 | Patti | G11B 5/022 |
| | | | | 360/68 |
| 6,594,517 | B1 * | 7/2003 | Nevo | A61B 5/4839 |
| | | | | 600/117 |
| 7,753,915 | B1 * | 7/2010 | Eksler | A61B 17/7016 |
| | | | | 606/86 R |
| 9,554,818 | B2 * | 1/2017 | Rohaninejad | A61B 17/282 |
| 10,737,398 | B2 * | 8/2020 | Remirez | A61B 34/30 |
| 2002/0103430 | A1 * | 8/2002 | Hastings | A61B 5/055 |
| | | | | 600/411 |
| 2003/0195412 | A1 * | 10/2003 | Gillies | A61B 5/055 |
| | | | | 600/407 |
| 2004/0050395 | A1 * | 3/2004 | Ueda | A61B 34/73 |
| | | | | 128/899 |
| 2004/0260172 | A1 * | 12/2004 | Ritter | A61M 25/0127 |
| | | | | 600/411 |
| 2006/0169293 | A1 * | 8/2006 | Yokoi | A61B 1/00158 |
| | | | | 128/899 |
| 2007/0088197 | A1 * | 4/2007 | Garibaldi | A61B 1/00158 |
| | | | | 604/95.01 |
| 2013/0046297 | A1 * | 2/2013 | Lingeman | A61B 17/221 |
| | | | | 606/41 |
| 2014/0243587 | A1 * | 8/2014 | Rohaninejad | A61B 17/122 |
| | | | | 600/37 |
| 2015/0351819 | A1 * | 12/2015 | Gustafson | A61B 17/8875 |
| | | | | 606/104 |
| 2017/0042410 | A1 * | 2/2017 | Hasegawa | A61B 1/00165 |
| 2017/0332883 | A1 * | 11/2017 | Omoto | A61B 1/00078 |
| 2020/0289229 | A1 * | 9/2020 | Denlinger | G06T 7/50 |
| 2022/0095947 | A1 * | 3/2022 | Highsmith | A61B 5/367 |
| 2022/0125509 | A1 * | 4/2022 | Govari | A61N 1/362 |
| 2024/0041550 | A1 * | 2/2024 | Sitti | A61B 18/1445 |
| 2024/0060770 | A1 * | 2/2024 | Ha | G01L 1/246 |

OTHER PUBLICATIONS

M.F. Phelan, III. et al.: "Heat-Mitigated Design and Lorentz Force-Based Steering of an MRI-Driven Microcatheter toward Minimally Invasive Surgery," Adv. Sci. 2022, 2105352, Feb. 3, 2022.

U.S. Appl. No. 17/816,779, filed Aug. 2, 2022, Metin Sitti, Martin Phelan.

\* cited by examiner

1

METHOD FOR CONTROLLING A MOVEMENT OF A MEDICAL DEVICE IN A MAGNETIC FIELD

TECHNICAL FIELD

The present disclosure relates to a method for controlling a movement of a medical device in a magnetic field.

Additionally or alternatively, the present disclosure may be directed to a medical device configured to be controlled by the method.

Additionally or alternatively, the present disclosure may relate to a data processing device configured to carry out the method at least partly.

Additionally or alternatively, a computer program may be provided, wherein the computer program comprises instructions which, when the program is executed by a computer, e.g., the data processing device, cause the computer to carry out the method at least partly.

Additionally or alternatively, a computer-readable (storage) medium may be provided, wherein the computer-readable medium comprises instructions which, when executed by a computer, cause the computer to carry out the method at least partly.

BACKGROUND

Any discussion of the related art throughout the specification should in no way be considered as an admission that such related art is widely known or forms part of common general knowledge in the field.

Widespread use of noninvasive medical imaging modalities in surgeries such as magnetic resonance imaging (MRI), X-ray, and ultrasound (US) has enabled the deployment of micron-sized surgical tools such as guidewires and catheters into narrow cavities within the body. The conventional method for gaining access into a vessel, known as the Seldinger technique, involves gaining access to a blood vessel through the use of a puncturing needle, steerable guidewire through the needle, and preshaped or steerable catheter passed over the guidewire.

However, various issues can still arise with this approach, such as vessel perforation, breakage of the device tip, kinking, looping, or loss of the guidewire.

Guidewires and catheters can also be subject to losses in manual torque transmission to the distal tip in tortuous vessels, which makes navigation more challenging, especially when encountering narrow vessels located at small angles.

Steerable (active) catheters and continuum robots offer an alternative to traditional passive guidewire-based catheter deployment techniques with improvements in maneuverability and remote manipulation.

The main challenge in active catheter design is transmitting force and torque through the soft slender body to actuate the catheter tip. Some systems use tendon-based force transmission. However, researchers have proposed many different alternative actuation mechanisms, such as multibackbone, concentric tubes, pneumatics, smart materials, hydraulics, magnetics, or hybrid approaches to overcome certain drawbacks of tendon-based systems.

Integration to existing medical imaging modalities is another crucial part of device design. X-ray imaging is currently the gold standard for real-time visualization during minimally invasive surgeries. Radiopaque catheters can be visualized easily in vascular structures filled with contrast agents. However, it is hard to visualize the effect of the intervention on soft tissue with X-ray imaging due to the poor soft-tissue contrast. Therefore, there is a growing interest in MRI-guided minimally invasive interventions due to the highsoft-tissue contrast of MRI images for visualizing blood vessels (such as within the brain of a human being) and tissue response as well as no ionizing radiation, real-time tool tracking capabilities, and physiological measurement capabilities (e.g., MM thermometry, diffusion, and perfusion).

However, MRI scanners impose new constraints on medical device design and actuation. First, the permanent high magnetic field limits material choices to nonmagnetic materials for device construction to avoid unintended magnetic force and torque. Second, large nonmagnetic metal objects cause imaging susceptibility artifacts. Third, the MRI scanner's radio-frequency (RF) pulses can induce heating within conductive materials found in medical tools.

Therefore, there are numerous studies on developing MR-compatible actuation techniques for device steering. These approaches include using smart materials, hydraulic, pneumatic, and MRI-driven (magnetic) actuation.

Thermal actuation involves the use of current to induce forces and motion using thermally active materials that are highly responsive to changes in temperature, such as shape memory alloys (SMAs).

SMAs can perform large deformations in small sizes for catheter steering. However, they generally require longer response times, demonstrate highly nonlinear behavior, and may cause safety risks of heating neighboring tissue.

Hydraulic actuation can transmit large forces through the slender catheter using fluid pressure. However, this fluid pressure over compliant continuum bodies causes radial expansion for positive pressures and buckling for negative pressures leading to stiffness variability and fatigue in the soft body.

MRI-driven actuation offers signific advantages over the aforementioned techniques due to its scalability, safety, response time (nearly instantaneous), accuracy (other methods experience nonlinearities in actuation), and degrees of freedom (DoF). In addition, MM-driven actuation can utilize imaging gradient coils user-controlled to generate spatial field gradients for steering a wireless robot or magnetic catheter tip in 3D.

However, embedding magnetic elements to catheters for gradient steering introduces significant MR image distortion and additional catheter weight and bulkiness.

Another MRI-driven actuation approach is mounting microcoils on the catheter tip for Lorentz force-based catheter steering using manually-wound or laser-machined microcoils.

Lorentz force-based steering approaches introduce less weight to the soft body due to the high force-to-weight ratio in comparison to gradient steering.

Moreover, the image distortion can be controlled since the image artifacts only occur when coils are activated.

Magnetically-assisted catheterization using microcoils has been shown to be faster than manual navigation using MR imaging guidance for larger angles and comparable to X-ray guidance.

However, microcoil-based Joule heating effects have been a major design concern. Prior research has shown tissue thermal injury occurs above local temperatures of 44° C. Catheter-integrated microcoil studies have indicated using currents inputs above 300 mA (1.2 W) can lead to vessel thrombus, vacuolization, and medial hemorrhage. Potential solutions have included integrating heat dissipation mechanisms, such as alumina to the catheter tip and passing saline coolant through the microcoil tip, or regulating current to less than 300 mA (1.2 W) with less than 1 min activation times.

However, such solutions introduce additional weight and bulkiness to the catheter tip, require flow through the catheter, limit working channel size, and constrain the time necessary for active steering in the workspace.

The above given description can be applied mutatis mutandis to endoscopes, like neuroendoscopes. Neuroendoscopy is a minimally invasive technique to visualize and treat areas of the central nervous system including the skull, brain, and spine. Currently, neuroendoscopic systems are used to treat many different kinds of cases, including intraventricular lesions, craniosynostosis, spinal lesions, and skull base tumors. To this end, both rigid and flexible endoscopes are utilized in surgical operations.

However, the standard rigid endoscopic tools have drawbacks such as limited field of view and risk of blunt force trauma. Neuronavigation may improve existing techniques, especially among patients with intraventricular pathologies. Additionally, flexible endoscopes have a better mobility range which may be critical in complex anatomies like ventricles.

Although the introduction of neuroendoscopy into surgical operations has made significant improvements over other traditionally invasive surgical approaches, there is still room for improvement including improved precision and less trauma to surrounding tissue.

It may be an object of the present invention to overcome or ameliorate at least one of the disadvantages of the prior art, and/or to provide a useful alternative.

SUMMARY

Provided is a first method for controlling a movement of a medical device in a magnetic field. The medical device comprises a set of coils.

The first method comprises determining a torque that needs to be applied onto the medical device such that the medical device carries out the movement.

The first method comprises determining a minimum current that needs to be supplied to each coil of the set of coils, respectively, to reach the determined torque by solving an optimization problem.

The first method comprises supplying the determined minimum current to each coil of the set of coils, respectively, such that the medical device carries out the movement.

The optimization problem (for determining the minimum current) may be defined as follows:

$$I^* = \operatorname*{argmin}_I \|\tau_{coils} - \tau_{des}\|^2 + \alpha \|I\|_R^2$$

wherein:

I may represent a current supplied to each coil of the set of coils, respectively, $\tau\_coils$ may represent a total torque generated by the set of coils when being supplied with the current I, $\tau\_des$ may represent the torque that needs to be applied onto the medical device such that the medical device carries out the movement, and R may represent a resistance of each coil of the set of coils.

Determining the torque may comprise solving a further optimization problem to minimize the torque to be applied onto the medical device such that the medical device carries out the movement.

The medical device may comprise a flexible substantially rod-shaped portion. Additionally or alternatively, the movement may comprise a deformation of said rod-shaped portion resulting in a movement of a tip of said rod-shaped portion.

Solving the further optimization problem may comprise determining the deformation of said rod-shaped portion that is needed for the movement of the tip of said rod-shaped portion from an actual location to a desired location such that a torque that is required for the deformation of said rod-shaped portion is minimized. Additionally or alternatively, solving the further optimization problem may comprise determining the torque that needs to be applied onto the medical device such that the medical device carries out the movement to be equal to the torque that is required for the deformation of said rod-shaped portion.

The deformation that is needed for the movement of the tip of said rod-shaped portion from the actual location to the desired location may be determined using a model, optionally a Cosserat model, depicting the nonlinear dynamics of said rod-shaped portion.

Additionally or alternatively, a second method for controlling a movement of a medical device in a magnetic field may be provided. The medical device comprises a set of coils. The above given description with respect to the first method applies mutatis mutandis to the second method, and vice versa.

The second method comprises determining a torque that needs to be applied onto the medical device such that the medical device carries out the movement. Determining the torque that needs to be applied onto the medical device comprises solving an optimization problem to minimize the torque that needs to be applied onto the medical device such that the medical device carries out the movement.

The second method comprises determining a current that needs to be supplied to the set of coils to reach the determined torque.

The second method comprises supplying the determined current to the set of coils such that the medical device carries out the movement.

The medical device may comprise a flexible substantially rod-shaped portion. Additionally or alternatively, the movement may comprise a deformation of said rod-shaped portion resulting in a movement of a tip of said rod-shaped portion.

Solving the optimization problem (for minimizing the torque) may comprise determining the deformation of said rod-shaped portion that is needed for the movement of the tip of said rod-shaped portion from an actual location to a desired location such that a torque that is required for the deformation of said rod-shaped portion is minimized. Additionally or alternatively, solving the optimization problem (for minimizing the torque) may comprise determining the torque that needs to be applied onto the medical device such that the medical device carries out the movement to be equal to the torque that is required for the deformation of said rod-shaped portion.

The deformation that is needed for the movement of the tip of said rod-shaped portion from the actual location to the desired location may be determined using a model, optionally a Cosserat model, depicting the nonlinear dynamics of said rod-shaped portion.

At least one of the above described methods may comprise receiving user input with respect to the movement via a user interface, optionally comprising a joystick. The user interface may be connected directly or indirectly, e.g., via a control unit, to the medical device.

At least one of the above described methods may comprise determining an actual position of the medical device, optionally the tip thereof, using medical imaging. Additionally or alternatively, at least one of the above described methods may comprise an automated controlling of the movement based on the determined actual position.

At least one of the above described methods may comprise displaying an actual position of the medical device, optionally a tip thereof, and/or a position of the medical device, optionally a tip thereof, after carrying out the movement on a display device. The display device may be connected to a medical imaging device.

At least one of the above described methods may comprise displaying the actual position of the medical device and/or the position of the medical device after carrying out the movement with respect to a tissue, optionally of a human being or an animal, on the display device.

In at least one of the above described methods the magnetic field may be produced by a medical imaging device, optionally a magnetic resonance imaging device.

In at least one of the above described methods the magnetic field may be a static magnetic field.

In at least one of the above described methods the medical device may comprise, optionally may be, a catheter, optionally an endovascular catheter.

The catheter may comprise a tip, optionally comprising a working channel extending through the tip of the catheter. Additionally or alternatively, the catheter may comprise the set of coils surrounding the tip. Additionally or alternatively, the catheter may comprise power wires arranged to supply the set of coils with electrical energy.

The set of coils may comprise four side coils arranged around the tip such that a straight line standing orthogonal on a longitudinal direction of the tip crosses a center of the respective side coil, i.e., the four side coils are arranged around the tip such that a magnetic flux direction of the four side coils points towards a center line of the tip.

A first and a second one of the side coils may be connected in series. Additionally or alternatively, a third and a fourth one of the side coils may be connected in series. Additionally or alternatively, the first and the second one of the side coils may be arranged on opposite sides of the tip. Additionally or alternatively, the third and the fourth one of the side coils may be arranged on opposite sides of the tip and in-between the first and the second one of the side coils.

A turn number of at least one of the four side coils may be between 2 and 40 (i.e, including 2 and 40). Optionally, the turn number of at least one of the four side coils may be between 4 and 30 (i.e, including 4 and 30). Optionally, the turn number of at least one of the four side coils may be 7.

The set of coils may comprise at least one axial coil arranged around the tip such that a straight line extending in parallel to the longitudinal direction of the tip crosses a center of the at least one axial coil.

At least one of the coils of the set of coils may be manufactured using laser machining, laser lithography and/or manually wound.

At least one of the coils of the set of coils may have, an optionally rectangular, Archimedean spiral coil design.

At least one of the coils of the set of coils may have an in-plane design.

The four side coils may be arranged on the same, optionally flexible, circuit board.

Additionally or alternatively, in at least one of the above described methods the medical device may comprise, optionally may be, an endoscope, optionally a neuroendoscope.

The endoscope may comprise a tip, optionally comprising a working channel extending through the tip of the endoscope. Additionally or alternatively, the endoscope may comprise the set of coils surrounding the tip. Additionally or alternatively, the endoscope may comprise power wires arranged to supply the set of coils with electrical energy.

The set of coils may comprise four side coils arranged around the tip such that a straight line standing orthogonal on a longitudinal direction of the tip crosses a center of the respective side coil.

A first and a second one of the side coils may be connected in series. Additionally or alternatively, a third and a fourth one of the side coils may be connected in series. Additionally or alternatively, the first and the second one of the side coils may be arranged on opposite sides of the tip. Additionally or alternatively, the third and the fourth one of the side coils may be arranged on opposite sides of the tip and in-between the first and the second one of the side coils.

A turn number of at least one of the four side coils may be between 2 and 40 (i.e, including 2 and 40). Optionally, the turn number of at least one of the four side coils may be between 4 and 30 (i.e, including 4 and 30). Optionally, the turn number of at least one of the four side coils may be 7.

The set of coils may comprise at least one axial coil arranged around the tip such that a straight line extending in parallel to the longitudinal direction of the tip crosses a center of the at least one axial coil.

At least one of the coils of the set of coils may be manufactured using laser machining, laser lithography and/or manually wound.

At least one of the coils of the set of coils may have, an optionally rectangular, Archimedean spiral coil design.

At least one of the coils of the set of coils may have an in-plane design.

The four side coils may be arranged on the same, optionally flexible, circuit board.

The endoscope may comprise an end effector connected to the tip of the endoscope.

The end effector may comprise a further set of coils for actuating the end effector.

The method may comprise actuating the end effector by applying a current to the further set of coils.

The end effector may comprise a grasper with two jaws connected pivotably to each other. Additionally or alternatively, the further set of coils may comprise at least one side coil arranged at each one of the two jaws, respectively.

Actuating the end effector may comprise opening and/or closing the jaws of the grasper by applying the current to the further set of coils. The opening may be a movement where the jaws of the grasper are moved away from each other by turning them around the pivotably connection and the closing may be a movement where the jaws of the grasper are moved towards each other by turning them around the pivotably connection.

The method may comprise ablating and/or killing tissue, optionally comprising tumor cells, using the Joule heating caused by the current supplied to the further set of coils for actuating the end effector, optionally for opening and closing the grasper.

The tip of the endoscope may comprise a camera. Additionally or alternatively, the tip of the endoscope may comprise an illumination device, optionally comprising a light emitting diode (LED). Additionally or alternatively, the tip of the endoscope may comprise an opening of an irrigation channel extending through the endoscope.

Additionally or alternatively the disclosure is directed to the use of a grasper of an endoscope, optionally a neuroendoscope, for cauterization. The endoscope comprises a tip, an end effector connected to the tip, and a set of coils arranged at the end effector. The cauterization comprises actuating the end effector by applying a current to the set of coils, and ablating and/or killing tissue, optionally comprising tumor cells, using the Joule heating caused by the current supplied to the set of coils for actuating the end effector. The above given description with respect to the endoscope applies mutatis mutandis to the use for cauterization thereof and vice versa.

Additionally or alternatively, a data processing device may be provided which is configured to carry out at least one of the above described methods at least partly.

Additionally or alternatively, a computer program may be provided, wherein the computer program may comprise instructions which, when the program is executed by a computer, e.g., the data processing device, cause the computer to carry out at least one of the above described methods at least partly.

Additionally or alternatively, a computer-readable (storage) medium may be provided, wherein the computer-readable medium comprises instructions which, when executed by a computer, cause the computer to carry out at least one of the above described methods at least partly.

In the following definitions of terms used in this description are given, wherein the respective description is just one possible specific definition out of many possible definitions of the respective term and is thus not intended to limit the scope of the disclosure to this specific definition.

Unless defined otherwise, all technical and scientific terms used herein have the same meaning as is commonly understood by one of ordinary skill in the art to which this disclosure belongs. In the event that there is a plurality of definitions for a term herein, those in this section prevail unless stated otherwise.

Where ever the phrase "for example", "such as", "including" and the like are used herein, the phrase "and without limitation" is understood to follow unless explicitly stated otherwise. Similarly "an example" "exemplary" and the like are understood to be non-limiting.

The term "substantially" allows for deviations from the descriptor that do not negatively impact the intended purpose. Descriptive terms are understood to be modified by the term "substantially" even if the word "substantially" is not explicitly recited.

The term "about" when used in connection with a numerical value refers to the actual given value, and to the approximation to such given value that would reasonably be inferred by one of ordinary skill in the art, including approximations due to the experimental and or measurement conditions for such given value.

The terms "comprising" and "including" and "having" and "involving" (and similarly "comprises", "includes", "has", and "involves") and the like are used interchangeably and have the same meaning. Specifically, each of the terms is defined consistent with the common United States patent law definition of "comprising" and is therefore interpreted to be an open term meaning "at least the following", and is also interpreted not to exclude additional features, limitations, aspects, etc. Thus, for example,"a device having components a, b, and c" means that the device includes at least components a, b and c. Similarly, the phrase: "a method involving steps a, b, and c" means that the method includes at least steps a, b, and c.

Unless the context clearly requires otherwise, throughout the description and the claims, the words "comprise","comprising", and the like are to be construed in an inclusive sense as opposed to an exclusive or exhaustive sense; that is to say, in the sense of "including, but not limited to".

The term "method" as used herein may include a computer-implemented method. The expression "computer-implemented method" covers claims which involve computers, computer networks or other programmable apparatus, whereby at least one feature is realised by means of a program. A computer-implemented method may be a method which is at least partly carried out by a data processing unit, e.g. a computer.

The term "controlling" may be defined as a process in a system in which one or more variables as input variables influence other variables as output variables due to the laws peculiar to the system. Additionally or alternatively, the term "controlling" may be defined as a process in which a variable, the controlled variable (the variable to be controlled), is continuously recorded, compared with another variable, the reference variable, and influenced in the sense of an adjustment to the reference variable.

The term "movement" may include any displacement or change of a position of a device, here the medical device, optionally the tip thereof. In one possible interpretation the movement may be a motion. A motion may be the phenomenon in which an object, here the medical device, optionally the tip thereof, changes its position with respect to space and time, optionally the magnetic field.

The term "determining" may include carrying out one or more mathematical operations in order to determine based on a given input in a given manner a desired output.

The term "torque" may be the rotational equivalent of a linear force. The term "torque" may be also referred to as the moment, moment of force, rotational force or turning effect. The torque may represent the capability of a force to produce change in the rotational motion of a body, such as the rode shaped portion of the medical device. The torque may be defined as the product of the magnitude of the force and the perpendicular distance of the line of action of the force from the axis of rotation. In three dimensions, the torque may be a pseudovector; for point particles, it is given by the cross product of the position vector (distance vector) and the force vector. The magnitude of torque of a rigid body may depend on three quantities: the force applied, the lever arm vector connecting the point about which the torque is being measured to the point of force application, and the angle between the force and lever arm vectors. The toque may be defined by the force that is applied to the tip of the medical device.

Instead of the term "current", the term "electric current" may be used. An electric current is a stream of charged particles, such as electrons or ions, moving through an electrical conductor or space. It is measured as the net rate of flow of electric charge through a surface or into a control volume. The moving particles are called charge carriers, which may be one of several types of particles, depending on the conductor. In electric circuits the charge carriers are often electrons moving through a wire. In semiconductors they can be electrons or holes. In an electrolyte the charge carriers are ions, while in plasma, an ionized gas, they are ions and electrons. The SI unit of electric current is the ampere, or amp, which is the flow of electric charge across a surface at the rate of one coulomb per second. Electric currents create magnetic fields, which may be are used to actuate or move the medical device in the (external) magnetic field. In ordinary conductors, they cause Joule heating.

Instead of the term "coil", the term electromagnetic coil may be used. An electromagnetic coil may be an electrical conductor such as a wire in the shape of a coil, spiral or helix. An electric current may be passed through the wire of the coil to generate a magnetic field. A current through any conductor creates a circular magnetic field around the conductor due to Ampere's law. One advantage of using the coil shape may be that it increases the strength of the magnetic field produced by a given current. The magnetic fields generated by the separate turns of wire all pass through the center of the coil and add (superpose) to produce a strong field there. The more turns of wire, the stronger the field produced may be and the stronger the effect of Joule heating may be.

An optimization problem may be described as the problem of finding substantially the best solution from all feasible solutions.

A medical device may be any device intended to be used for medical purposes. According to one possible definition a medical device may be an instrument, apparatus, implement, machine, contrivance, implant, in vitro reagent, or other similar or related article, including a component part, or accessory which is intended for use in the diagnosis of disease or other conditions, or in the cure, mitigation, treatment, or prevention of disease, in man or other animals, and/or intended to affect the structure or any function of the body of man or other animals, and which does not achieve its primary intended purposes through chemical action within or on the body of man or other animals and which is not dependent upon being metabolized for the achievement of its primary intended purposes. The term "medical device" may or may not include software functions. According to another possible definition the term "medical device" may mean any instrument, apparatus, appliance, software, material or other article, whether used alone or in combination, including the software intended by its manufacturer to be used specifically for diagnostic and/or therapeutic purposes and necessary for its proper application, intended by the manufacturer to be used for human beings or animals for the purpose of diagnosis, prevention, monitoring, treatment or alleviation of disease, diagnosis, monitoring, treatment, alleviation of or compensation for an injury or handicap, investigation, replacement or modification of the anatomy or of a physiological process, and/or control of conception, and which does not achieve its principal intended action in or on the human and/or animal body by pharmacological, immunological or metabolic means, but which may be assisted in its function by such means.

Instead of the term "resistance", the term "electrical resistance" may be used. The resistance multiplied by the current may be equal to the (electrical) voltage.

A rod-shaped portion may be a portion or part of the medical device that may have a substantially circular cross section. The rod-shaped portion may have cylindrical form wherein a height or length of the rod-shaped portion exceeds the diameter of the rod-shaped portion. The tip of the rod-shaped portion may be outermost part of the rod-shaped portion in a forward direction of the medical device. The tip of the rod-shaped portion may comprise a region around the circumference at or near the end of the outermost part of the rod-shaped portion. The rod-shaped portion may comprise or may be realized using a tube. The tip may be called insertion tip of the medical device.

The Cosserat model may be based on the Cosserat rod theory. This approach may allow for a substantially exact solution to the static of a continuum robot, as it is not subject to any assumption. It solves a set of equilibrium equations between position, orientation, internal force and torque of the robot, here the medical device, optionally the rod-shaped portion thereof. Creating an accurate model that can predict the shape of a continuum robot allows to properly control the robot's shape.

A catheter may comprise a thin tube made from medical grade materials serving a broad range of functions. Catheters are medical devices that can be inserted in the body to treat diseases and/or perform a surgical procedure. By modifying the material or adjusting the way catheters are manufactured, it is possible to tailor catheters for cardiovascular, urological, gastrointestinal, neurovascular, and ophthalmic applications. The process of inserting a catheter is "catheterization". A catheter may comprise a thin, flexible tube ("soft" catheter) through catheters are available in varying levels of stiffness depending on the application. This may be taken into account by the (Cosserat) model. The catheter my be configured to be inserted into a body cavity, duct, or vessel, brain, skin or adipose tissue. Functionally, the catheter may allow drainage, administration of fluids or gases, access by surgical instruments, and/or perform a wide variety of other tasks depending on the type of catheter. The catheter may be a so called probe used in preclinical or clinical research for sampling of lipophilic and hydrophilic compounds, protein-bound and unbound drugs, neurotransmitters, peptides and proteins, antibodies, nanoparticles and nanocarriers, enzymes and vesicles.

An endovascular catheter may be a catheter configured to be used for endovascular aneurysm repair (EVAR) which is a type of minimally-invasive endovascular surgery used to treat pathology of the aorta, most commonly an abdominal aortic aneurysm (AAA). When used to treat thoracic aortic disease, the procedure is then specifically termed TEVAR for "thoracic endovascular aortic/aneurysm repair." The procedure may involve the placement of an expandable stent graft within the aorta to treat aortic disease without operating directly on the aorta.

An endoscope is a medical device that may be used as an inspection instrument. An endoscope may comprise an image sensor, an optical lens, a light source and/or a mechanical device, which is used to look deep into the body by way of openings such as the mouth or anus.

A neuroendoscope may be an endoscope configured to be used for neuroendoscopy which is a minimally invasive surgical technique that allows inspection (and optionally illumination) of angles in hidden parts of the surgical field, enabling optionally clear visualization and manipulation of anatomical structures. There are three main subdisciplines of endoscopic neurosurgery: intraventricular neuroendoscopy for the treatment of occlusive hydrocephalus and other lesions within and around the ventricular system, transnasal neuroendoscopy including the different endoscopic endonasal approaches for pituitary and further skull base pathologies, as well as transcranial endoscope-assisted microneurosurgery for various kinds of intracranial tumors, cysts and neurovascular lesions. However, it has to be noted that the present disclosure is not limited to these three fields.

A medical imaging device may be a device configured to be used for medical imaging. Medical imaging is the technique and process of imaging the interior of a body. Medical imaging may incorporate radiology, which uses the imaging technologies of X-ray radiography, magnetic resonance imaging, ultrasound, endoscopy, elastography, tactile imaging, thermography, medical photography, and/or nuclear medicine functional imaging techniques as positron emission tomography (PET) and single-photon emission computed tomography (SPECT).

A magnetic resonance imaging device is a medical imaging device configured to be used in magnetic resonance imaging (MM) which is a medical imaging technique that may be used in radiology to form pictures of the anatomy and the physiological processes of the body. Mill scanners use strong magnetic fields, magnetic field gradients, and radio waves to generate images of the organs in the body.

A working channel may be a channel, optionally having a circular shape form, arranged in the rod-shaped portion of the medial device. The working channel may extend throughout the whole rod shaped portion. The working channel may be used to transport a (medical) device, a gas and/or a fluid from one end of the medical device, optionally located outside of the body, to the tip of the rod-shaped portion. The working channel may house or accommodate devices permanently and/or temporarily, such as a camera, an electrical wire and/or a light source, at least partly.

Cauterization may be defined as the action of burning body tissue using heat, to stop an injury from bleeding or getting infected, and/or to remove harmful cells.

DESCRIPTION OF EXEMPLARY EMBODIMENTS

As required, detailed embodiments are disclosed herein; however, it is to be understood that the disclosed embodiments are merely exemplary of the invention that may be embodied in various forms. The figures are not necessarily to scale, and some features may be exaggerated to show details of particular components. Therefore, specific structural and functional details disclosed herein are not to be interpreted as limiting, but merely as a basis for the claims and as a representative basis for teaching one skilled in the art to variously employ the present invention.

In the following a solution to the Lorentz force-induced heating concern without using active cooling or limiting microcoil activation times for steering of a medical device is described. This is accomplished using a heat-mitigated design and actuation strategy using the previously mentioned 44° C. as a heating threshold for safe navigation within the body (assuming no arterial flow; worst-case scenario).

Figure 1:
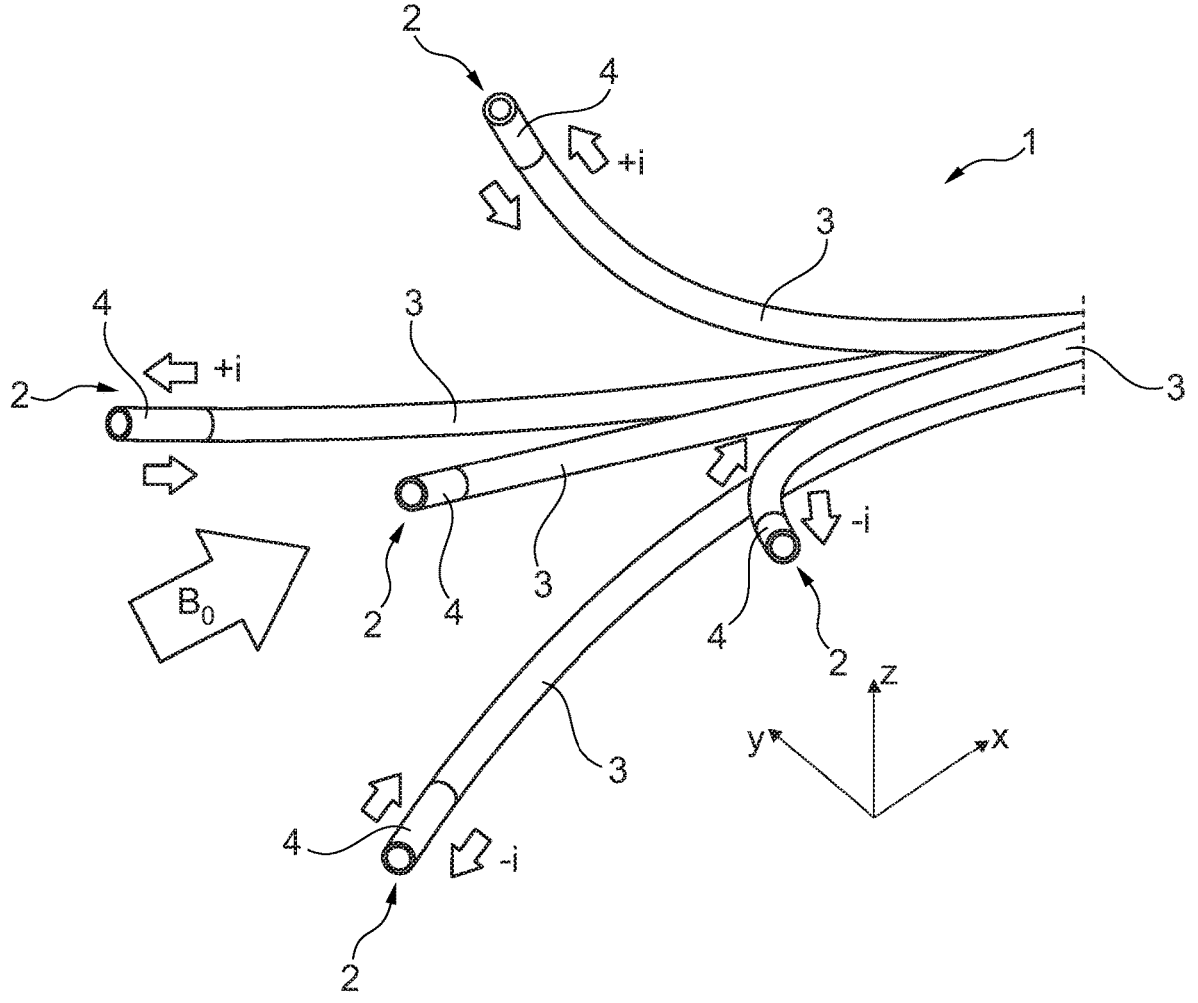
FIG. 1 shows schematically, in a perspective view a catheter in an initial position and four position being different from the initially position.

In FIG. 1 a catheter 1 is shown in a perspective view in five different states/positions. Furthermore a cartesian coordinate system is shown comprising a X-axis, a Y-axis and a Z-Axis, wherein an angle between these axes is 90°, respectively. A magnetic field comprising a magnetic field vector $B_0$ aligned in parallel to the X-axis is present.

The catheter 1 comprises a rod-shaped portion 3 and a tip 2 arranged at a distal end of the rod-shaped portion 3, wherein a set of coils 4 is arranged at the tip 2.

Figure 3:
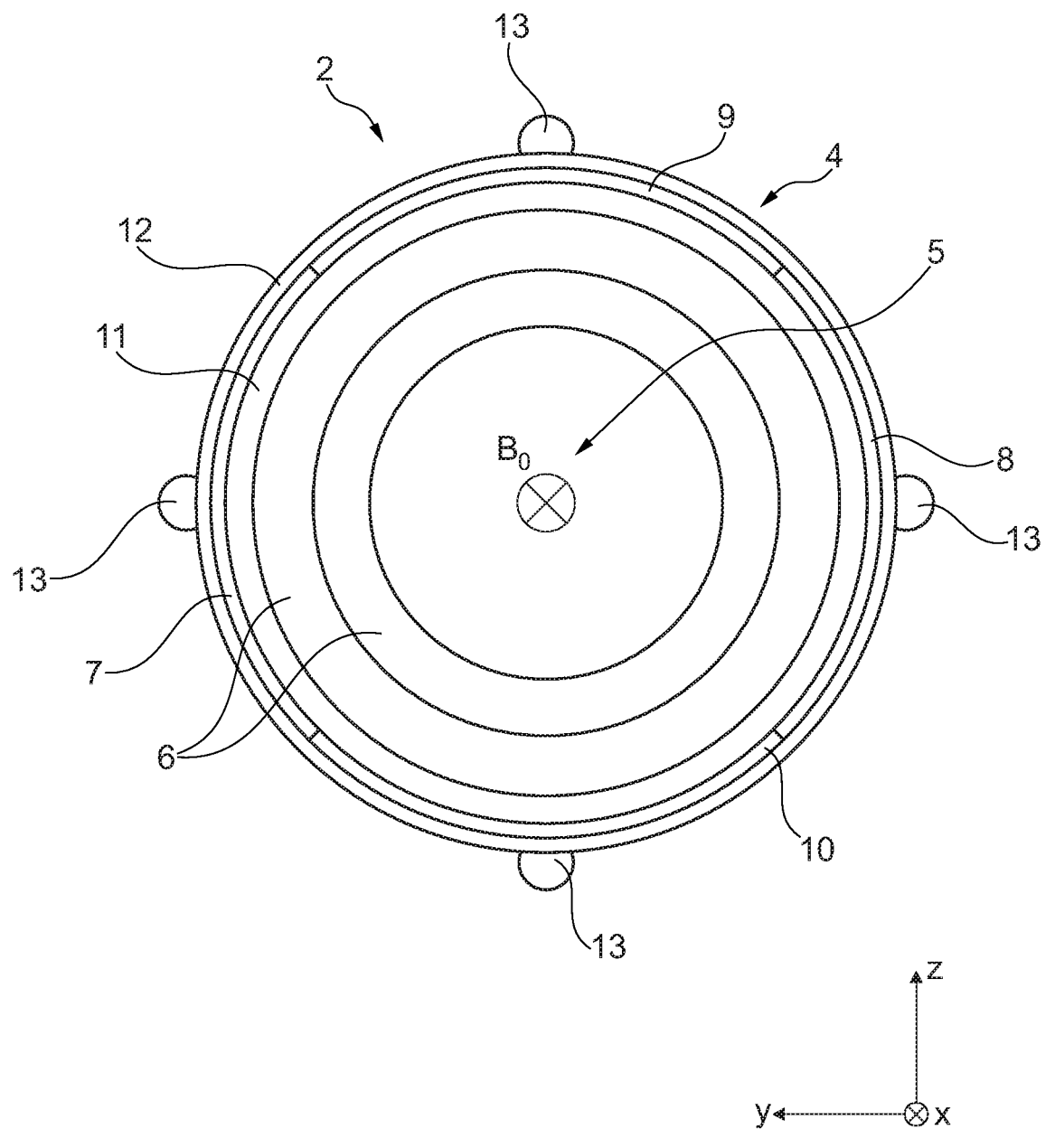
FIG. 3 shows schematically a cross sectional view of a tip of the catheter of FIG. 1.

As can be gathered from FIG. 3, which is a cross sectional view of the cylindrical tip 2, the catheter 1 comprises a working channel 5 having a round cross section and extending from the tip 2 through the rod-shaped portion 3 such that devices, tissue etc. may be brought from outside a body in which the catheter 1 is located through the working channel 5 into the body and vice versa.

As in FIG. 1, also in FIG. 3 a cartesian coordinate system is shown comprising a X-axis, a Y-axis and a Z-Axis, wherein an angle between these axes is 90°, respectively. The position of the axes X, Y, Z in FIG. 3 corresponds to the initial/middle position of the catheter 1 in FIG. 1. Therefore, the X-axis is arranged in parallel to a longitudinal direction of the tip 2 and of the working channel 5.

The set of coils 4 comprises two axial coils 6 having a round cross section and which are arranged around the working channel 5, wherein a center of these two axial coils 6 is located on the X-axis, i.e., windings of the axial coils 6 are wound around the X-axis. In other words, a straight line extending in parallel to the longitudinal direction of the tip 2 crosses the center of the two axial coils 6. Therefore, in the initial position of the catheter 1 shown in FIGS. 1 and 3, where the magnetic field vector $B_0$ extends in parallel to the X-axis, no Lorenz force may be generated by the axial coils 6.

The set of coils 4 comprises four side coils 7-10 arranged around the two axial coils 6 of tip 2 such that a straight line standing orthogonal on the longitudinal direction of the tip 2, i.e., a straight line arranged in the YZ-plane and standing orthogonal on the X-axis, crosses a center of the respective side coil 7-10. Therefore, in the initial position of the catheter 1 shown in FIGS. 1 and 3, where the magnetic field vector $B_0$ extends in parallel to the X-axis, a Lorenz force may be generated by the side coils 7-10 when applying a current to them. To do so, the catheter 1 comprise power wires 13 arranged at an outer circumference of a isolation material 12 (which surrounds the side coils 7-10) of the tip 2 to supply the set of coils 4 with electrical energy.

Figure 2:
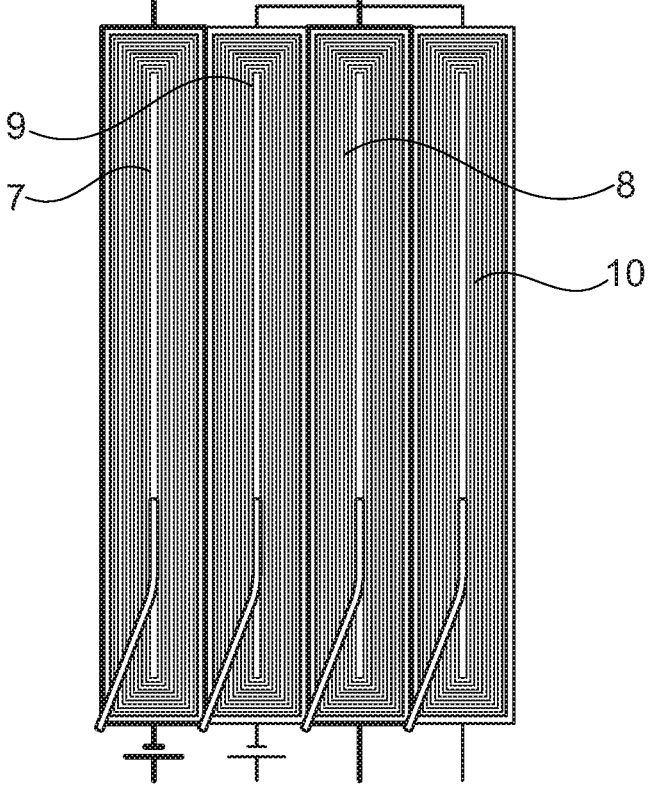
FIG. 2 shows schematically side coils of the catheter of FIG. 1.

All side coils 7-10 are arranged on the same flexible circuit board 14 which is wrapped around the axial coils 6, wherein a polymide layer 11 is arranged between the side coils 7-10 and the axial coils 6 (see FIG. 3). As can be gathered from FIG. 2, the first and a second one of the side coils 7, 8 are connected in series and the third and the fourth one of the side coils 9, 10 are also connected in series. As can be gathered from 3, the first and the second one of the side coils 7, 8 are arranged on opposite sides of the tip 2 and also the third and the fourth one of the side coils 9, 10 are arranged on opposite sides of the tip 2, i.e., the first and the second side coil 7, 8 are arranged in-between the third and the fourth side coil 9, 10.

The Lorentz force that is generated by the side coils 7-10 leads to a movement of the tip 2 of the catheter 1 substantially in the YZ-plane, as shown in FIG. 1. Depending on the direction/polarity of the current (indicated by +I and −I in FIG. 1) supplied to the side coils 7-10, the tip 2 moves to the left or the right when current is supplied to the first and the second side coil 7, 8 and up or down when current is supplied to the third and the fourth side coil 9, 10. Of course these movements may be combined, e.g., moving the tip 2 simultaneously up and to the right. Therefore, with this quad coil design, four digress of freedom may be realized.

When an angle of 90° is reached, i.e., when the rod-shaped portion 3 is bound to such an extent that the tip 2 magnetic field vector $B_0$ and the center of side coils 7-10 are in parallel, no Lorentz force is generated by the side coils 7-10 and the axial coils 6 may be used to overcome this point.

A turn number of the four side coils 7-10 may be between 2 and 40 (i.e, including 2 and 40) or between 4 and 30 (i.e, including 4 and 30), respectively. However, in the present case the turn number the four side coils 7-10 is 7 (seven), respectively. Together with the rectangular Archimedean spiral, in plane coil design of the side coils 7-10, which are manufactured using laser machining, a very small tip 2 diameter may be reached, e.g., around 1 mm.

This will be explained in detail below with respect to one specific implementation of the disclosure which is described solely for explanatory purposes and is not intended to limit the scope of the disclosure, especially the claims, in any way.

Lorentz-force actuators have proven to be effective for various robotic/medical applications due to their precision, high force output, and scalability for soft device integration. These actuators utilize external magnetic fields to generate a force directly controlled for robotic actuation. Therefore, Lorentz-force actuators can utilize the high external magnetic field such as generated in MRI environments to develop robotic devices.

It has been demonstrated integrating such actuators to catheters through the use of copper coils for Lorentz force-based steering in blood vessels and the heart. In this approach, controlling microcoil current polarity directly translates to a tip deflection of the tip 2 in the respective direction (se FIG. 1). The generated magnetic moment, m, and corresponding torque, T, can be determined in terms of the number of coil loops, N, current, I, and area normal vector, A, of a coil loop, and magnetic field vector (e.g., within an MR scanner) ($B_0=(0, 0, B_0)$), where $B_0$ is the (e.g., uniform, permanent, i.e., static) magnetic field (e.g., inside the MRI). This relation is represented as (Equation 1)

$$T = m \times B_0 = NI(A \times B_0)$$

which can be used to govern axial coil torque for a Lorentz force-actuated catheter with equally-sized coil loops. In terms of saddle (side) coil implementation, microcoils can be integrated to the catheter tip for additional degrees of freedom (DoF). Design optimization of an (e.g., MRI-driven) catheter 1 using a four coil configuration allowed for maximizing the achievable workspace (e.g., within the heart) given certain constraints such as the number of coil sets and current inputs.

However, maximizing the number of coil turns and area may not be feasible for navigating within narrow vasculature. In order to improve upon both existing design schemes, laser machining may be used in conjunction with the Archimedean spiral coil design to create an in-plane, quad-configuration, microcoil design shown in FIG. 2.

The proposed design enables more compact and significantly smaller final catheter diameters, e.g., down to 1 mm, than previously proposed designs while achieving comparable steerability. In this approach, both saddle/side coil sets are integrated on the same circumferential plane without introducing additional layer thickness compared to the state of the art.

The governing equations for a rectangular Archimedean spiral are given below for estimating the microcoil's magnetic moment. The approximate effective area of all coil loops 7-10 can be expressed as (Equation 2)

$$A_{total} = \sum_{i=0}^{N-1} (L_c - w - i(w + 2t))(W_c - w - i(w + 2t))$$

and corresponding total wire length for estimating power consumption as (Equation 3)

$$L_{coil} = \sum_{i=0}^{N-1} 2(W_c + L_c - 2i(2t + w) - 2w)$$

Inserting Equation (2) into Equation (1) yields the magnetic moment of a single saddle coil $$m = IA_{total}$$

Achieving higher bending angles for Lorentz force-based actuation implies maximizing the coil's magnetic moment. As shown in the above equations, tuning various parameters (i.e., coil turn number, current, catheter diameter) can influence the performance. Typically, a larger coil turn number implies better bending performance due to the increasing coil area. However, when power is constrained to the heating threshold (e.g., 0.5 W) to mitigate heating effects, an inverse relation exists between the magnetic moment and coil turn number. In other words, a lower coil turn number is ideal for mitigating heat but requires higher currents to generate such magnitudes of electromagnetic torque leading to undesirable heating within the power wires 13. However, using larger power wires 13 to mitigate heating increases flexural rigidity depending upon wire gauge and thus has undesirable effects on catheter steerability. Therefore, a microcoil turn number in the above description ranges, especially of approximately 7, may be used to maximize the magnetic moment while remaining within well-established current ratings for power wires 13 and an acceptable range of stiffness for (e.g., endovascular) catheters.

Figure 4:
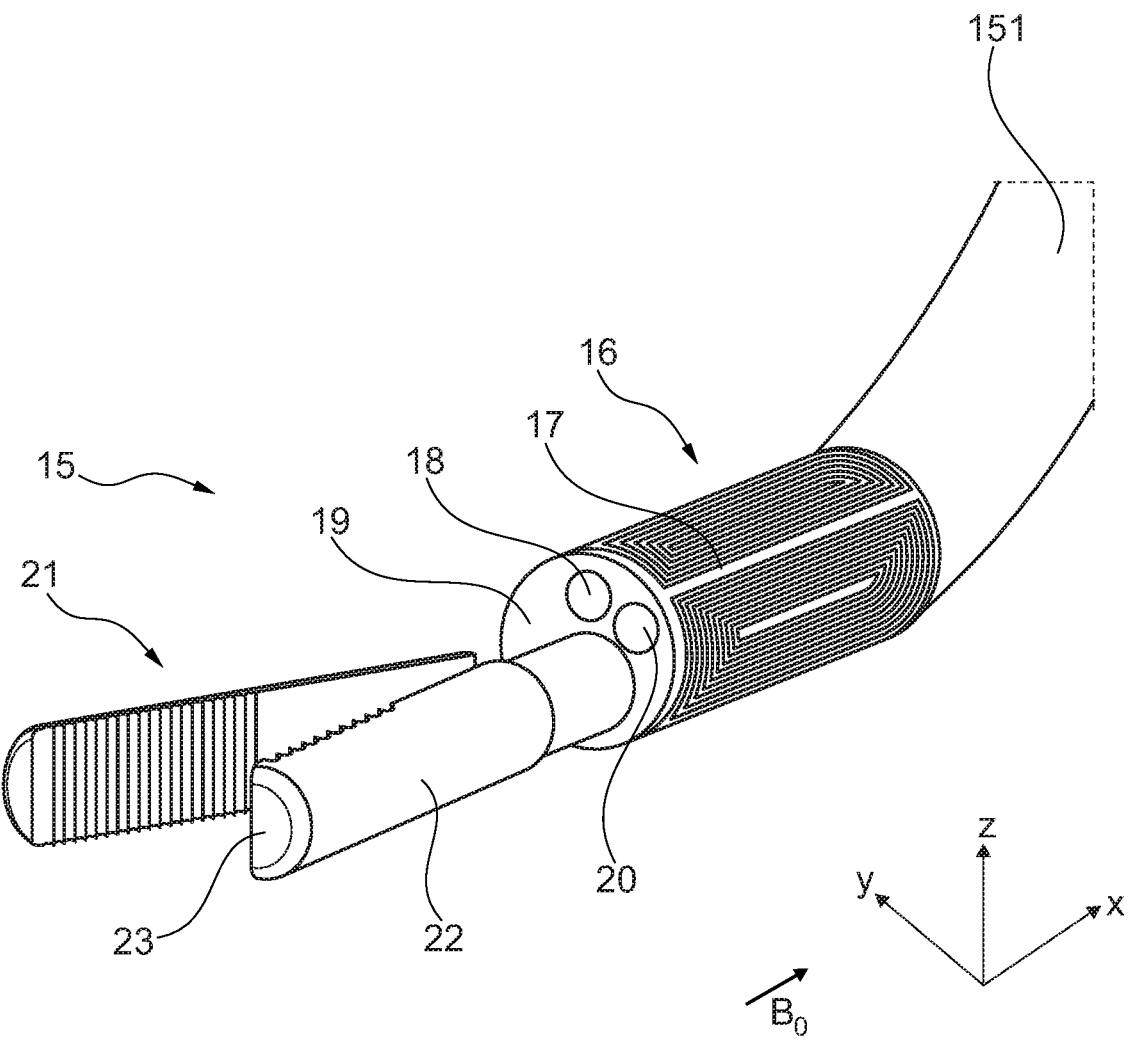
FIG. 4 shows schematically, in a perspective view an endoscope.

In the following an endoscope 15, here a neuroendoscope, that makes use of the same quad coil design as the catheter 1 is described in detail with respect to FIG. 4. The above given description applies mutatis mutandis to the endoscope 15 and is thus not repeated. Also here a cartesian coordinate system is shown comprising a X-axis, a Y-axis a and a Z-Axis, wherein an angle between these axes is 90°, respectively. A magnetic filed comprising a magnetic field vector $B_0$ aligned in parallel to the X-axis is present.

The endoscope 15 comprise a tip 16, a rod-shaped portion 151, a set of coils 17 surrounding the tip 16 which was already described above with respect to the set of coils 4 surrounding the tip 2 of the catheter 1 and (not shown) power wires arranged to supply the set of coils 17 with electrical energy in the same manner as the above described power wires 13 of the catheter 1. The tip 16 of the endoscope 15 comprises a camera 18, an illumination device 19, optionally comprising an LED, and an opening 20 of an irrigation channel extending through the endoscope 15.

The endoscope 15 comprises an end effector 21, here a grasper, connected to the tip 16 of the endoscope 15 The end effector is Lorentz force-actuated. Therefore, the grasper 21 comprises a further set of coils 22 for actuating jaws 23 of the grasper 21.

Figure 5:
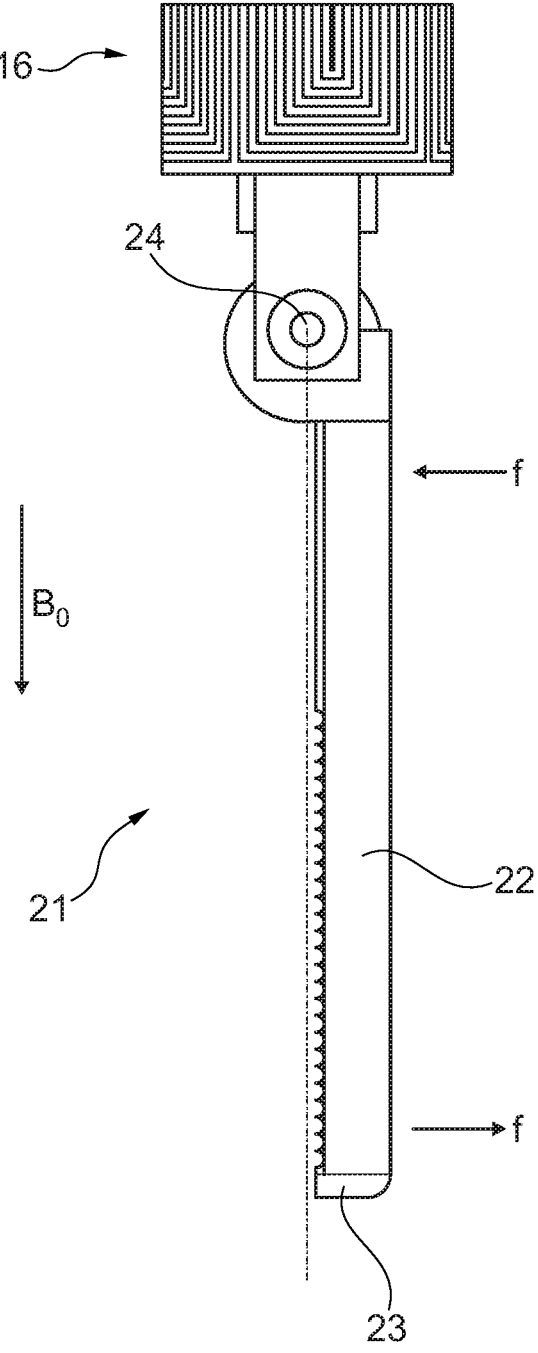
FIG. 5 shows schematically, in a top view a grasper of the endoscope of FIG. 4 in a closed state.
Figure 6:
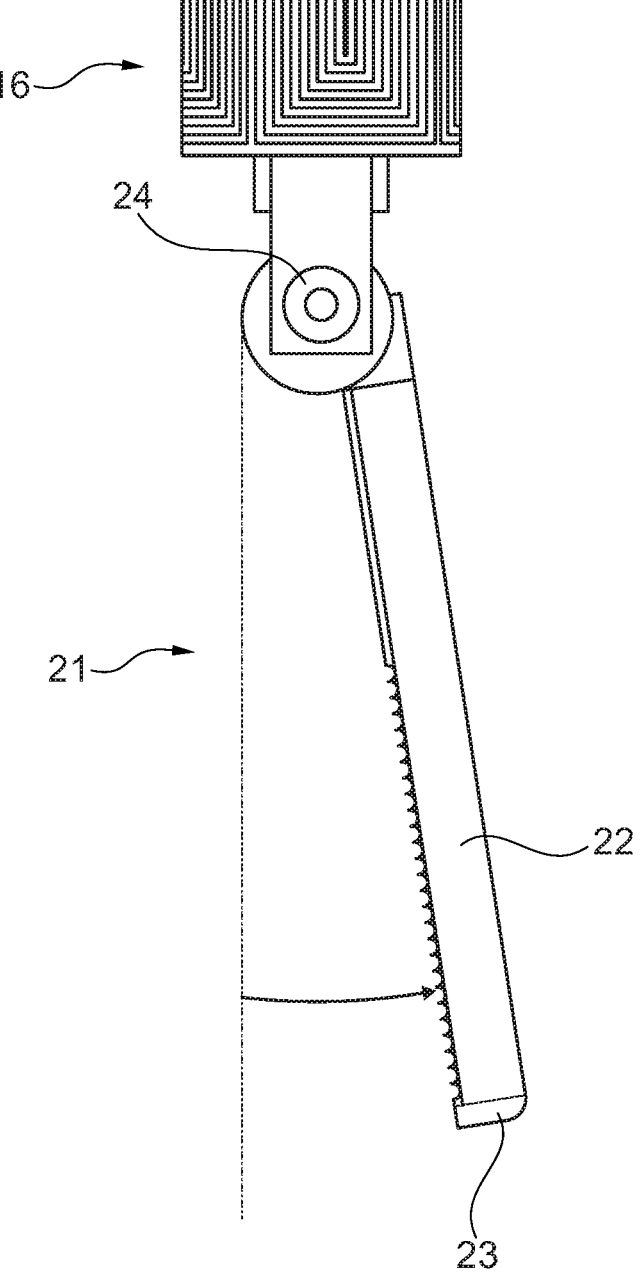
FIG. 6 shows schematically, in a top view the grasper of the endoscope of FIG. 4 in an open state.

This is shown in detail in FIGS. 5 and 6. The two jaws 23 (only one is shown in FIGS. 5 and 6) are connected pivotably via a pivot joint 24 to each other. The further set of coils 22 comprises a side coil arranged at each one of the two jaws 23 such that by applying a current to the side coils of the further set of coils 22 the jaws 23 may be open and or closed by turning them around the pivot about joint 24 (FIG. 5 shows the closed and FIG. 6 the open state).

Figure 7:
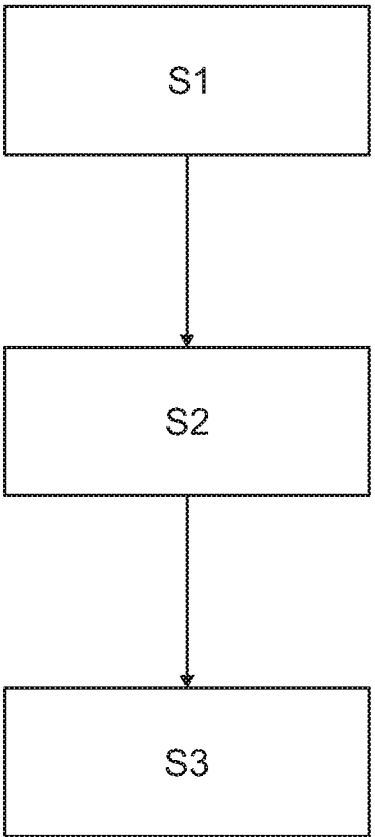
FIG. 7 shows a flow diagram of a method for controlling a movement of a medical device in a magnetic field.

In the following a method for controlling a movement of the above described medical devices, i.e, the endoscope 15 and the catheter 2, in a magnetic field is described in detail. A flow chart of the method is shown in FIG. 7. The method is beneficial since Joule heating may remain a concern even with the above described design of the medical devices and therefore optimizing microcoil (saddle/axial) power distribution may impact the performance of the medical device 1, 15.

Both medical devices 2, 15 have in common that they comprise a flexible substantially rod-shaped portion 3, 151. The movement of the tip 2, 16 comprises a deformation of said rod-shaped portion 3, 151 resulting in a movement of the tip 2, 16 of said rod-shaped portion 3, 151. Therefore, the principles described below may be applied to both, the catheter 2 and the endoscope 15.

In a first step S1 of the method a torque that needs to be applied onto the medical device 1, 15 such that the tip 2, 16 of the medical device 1, 15 carries out the movement is determined.

Determining the torque may comprise solving a first optimization problem to minimize the torque to be applied onto the medical device 1, 15 such that the tip 2, 16 of the medical device 1, 15 carries out the movement.

Solving the first optimization problem may comprise determining the deformation of said rod-shaped portion 3, 151 that is needed for the movement of the tip 2, 16 of said rod-shaped portion 3, 151 from an actual location to a desired location such that a torque that is required for the deformation of said rod-shaped portion 3, 151 is minimized. The torque that needs to be applied onto the medical device 1, 15 such that the medical device carries out the movement is then set to be equal to the torque that is required for the deformation of said rod-shaped portion 3, 151.

The deformation that is needed for the movement of the tip 2, 16 of said rod-shaped portion 3, 151 from the actual location to the desired location may be determined using a model, optionally a Cosserat model, depicting the nonlinear dynamics of said rod-shaped portion 3, 151.

This will be explained in detail below with respect to one specific implementation of the disclosure which is described solely for explanatory purposes and is not intended to limit the scope of the disclosure, especially the claims, in any way.

Steerable catheters undergo large deformations/motions during surgical procedures. One method of modeling such motions commonly used to model elastic rods and continuum rods is the Cosserat rod theory. The Cosserat rod model integrates the traditional bending and twisting of Kirchhoff rods with additional stretching and shearing to capture full beam dynamics. The Cosserat model accurately depicts the nonlinear dynamics of elastic rods with different materials and geometries. The catheter 1 may be modeled as a cantilever beam undergoing an external torque and tip force. The state of the catheter may be described using a set of N discretized segments $Y=[y_0^T, y_1^T, \ldots, y_N^T]_N^T$. The discretized state vector for each segment i contains segment position ($p_i \in R^3$), orientation ($R_i \in SO(3)$), extension force ($n \in R^3$), and shear torque ($m \in R^3$), which can be expressed in one vector $y_i=[p_i, R_i, n_i, m_i]$. The rotation matrix is defined in the (e.g., MRI's) fixed coordinate frame, along with two additional coordinate frames L; control frame C representing the catheter free length starting position and tip frame T locating the start of the microcoils. Therefore, a system of nonlinear ordinary differential equations (ODEs) can be expressed as (Equations 5 to 8)

$$\dot{P}_i = R_i v_i$$

$$\dot{R}_i = R_i u_i$$

$$\dot{n}_i = -\rho A g$$

$$\dot{m}_i = -\dot{p}_i \times n_i$$

where v and u are tangent and curvature vectors defined as, $v=\hat{z}+K_1 R^T n$ and $u=K_2 R^T m$ m, where $\hat{z}$ is the unit vector in local coordinate frame, $K_1=diag(GA,GA,EA)$ and $K_2=diag(EI_A, EI_A, GJ)$. G, A, E, $I_A$, and J represent the shear modulus, cross-sectional area, elastic modulus, area moment of inertia, and polar moment of inertia, respectively. Catheter forward kinematics, $Y=f(n_0, m_0)$, can be calculated through numerical integration using fourth order Runge—Kutta algorithm, given the catheter's initial conditions: $R_0=R_C$, $p_0=p_C$, $n_0=n_C$, $m_0=m_C$. Although the forward kinematic model in an initial value problem form is useful for simulating catheter motion given a base wrench, an inverse kinematic model is needed to determine the minimum catheter torque for reaching desired orientations. An inverse kinematic model in a boundary value problem (BVP) form may be formulated with the following boundary conditions: $R_0=R_C$, $p_0=p_C$, $n_\tau=0$, $m_\tau=\tau_{des}$ and $R_\tau=R_{des}$. Here, $n_\tau$ and $m_\tau$ are expressed as the magnetic wrench at the tip 2 of the catheter 1. Due to the negligible magnetic gradient pulling force acting on the catheter tip in comparison to the magnitude of a distributed Lorentz force, it is assumed there is only torque at the tip 2. Therefore, the inverse kinematic for desired tip torque ($\tau_{des}=IK(R_{des})$) is calculated by solving the following optimization problem for tip torque (Equation 9)

$$\underset{Y}{argmin} \|R_{\tau,des} \boxminus R_\tau\|_2^2 + \|\tau_{des}\|_2^2$$

$$s.t. \ Y = f(n_0, m_0)$$

where the box minus ( $\boxminus$: $SO(3) \times SO(3) \to \mathbb{R}^3$) is the rotation difference operator based on the matrix logarithm defined in Lie algebra. Tip torque is $\tau_{des}=m_N$. Optimization is solved in real-time using the iterative Levenberg—Marquardt method implemented in C++, where catheter forward kinematics is used as the shooting function. It is important to note that the $\boxminus$ error may be essential for the stability of the solution for near singular values, and the quadratic on tip torque regularizes the cost function to eliminate inverse kinematic solutions with loops. The above given description applies mutatis mutandis to the endoscope.

In a second step S2 of the method a minimum current that needs to be supplied to each coil 6, 7-10 of the set of coils 4, 17, to reach the determined torque ($\tau\_des$) by solving a second optimization problem is determined, respectively.

This will be explained in detail below with respect to one specific implementation of the disclosure which is described solely for explanatory purposes and is not intended to limit the scope of the disclosure, especially the claims, in any way.

Microcoil-based heat generation can be reduced by optimally distributing current to the side and axial coils 6, 7-10.

Figure 8:
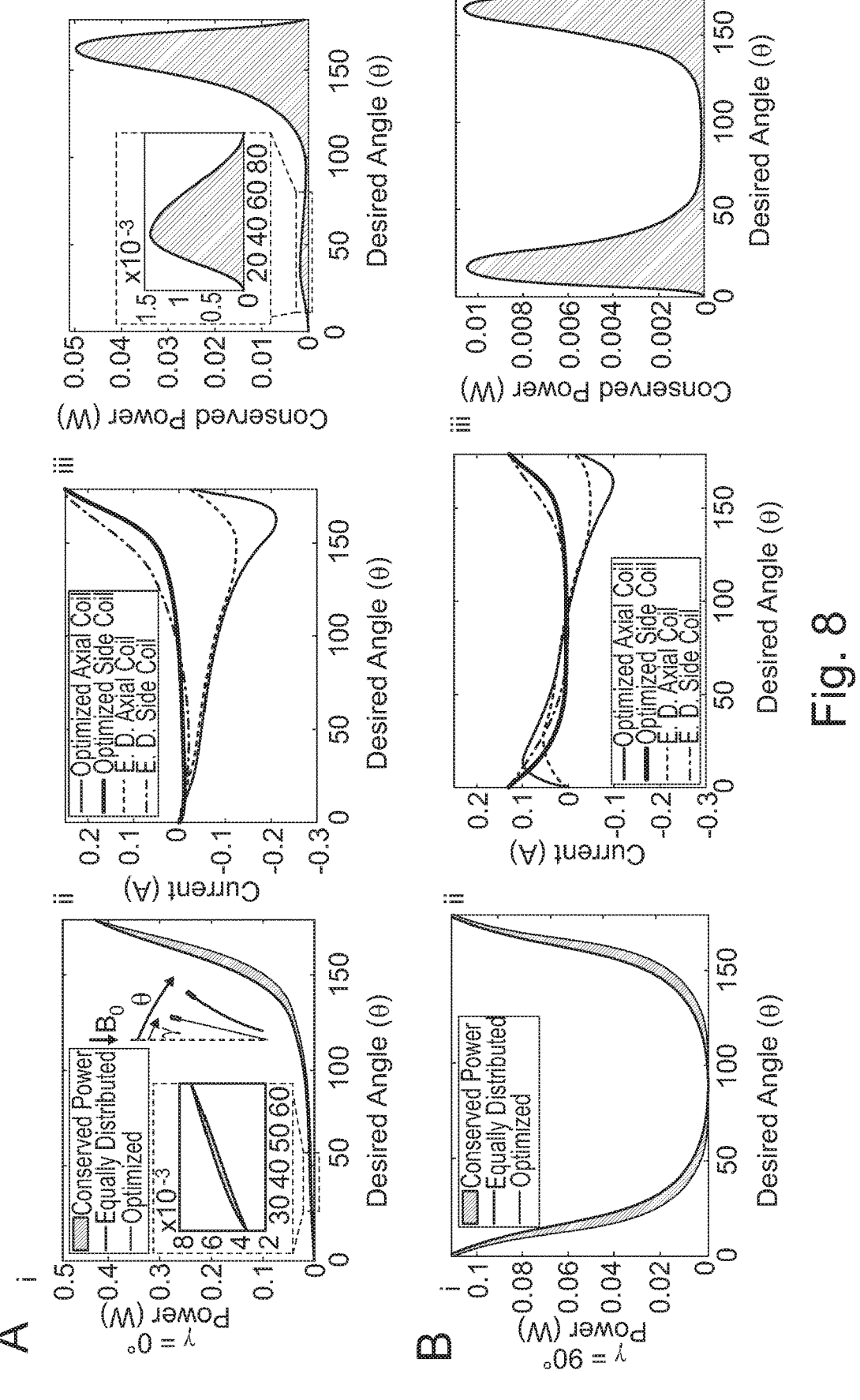
FIG. 8 shows diagrams for illustrating power-optimized controller capabilities at various initial orientations and their corresponding Joule heating effects when coils are powered.

The tip orientation controller therefore comprises a two-stage optimization scheme: 1) inverse kinematics to determine torque using Equation (9), and 2) saddle/axial coil current distribution. A power-optimized current distribution problem is formulated as a non-linear quadratic optimization (Equations 10 and 11)

$$I^* = \underset{I}{\operatorname{argmin}} \|\tau_{coils} - \tau_{des}\|^2 + \alpha \|I\|_R^2$$

$$\text{s.t. } \tau_{coils} = \tau_{side,1} + \tau_{side,2} + \tau_{axial}$$

where $I=[I_{side,1}, I_{side,2}, I_{axial}]$ represents the saddle/sie and axial coil currents, and $\tau_{coil}$ represents the total torque generated by a saddle and axial coilset 6, 7-10, respectively. The first term of the costfunction is for consistency between desired tip torque and total coil torque, and second term is the coil power consumption cost, where R=diag($R_{side,1}$, $R_{side,2}$, $R_{axial}$] is the resistance of the coils. Due to the difference in magnitude between torque error and induced currents, an a constant is incorporated (determined using a grid search to find the best fitting; $1 \times 10^{-6}$). This optimization is also solved using the Levenberg—Marquardt method. A comparison between actuating coils using equally-distributed power versus the optimal approach is shown in FIG. 8. In FIG. 8A-i) defines the initial angle between the catheter tip 2 and B$_0$ field vector, $\gamma$, and final tip orientation, $\theta$, upon excitation. A,B) represent when the quad-configuration microcoil (QCM) begins aligned with and perpendicular to the B$_0$ field, respectively. Power was compared between both actuation schemes in (A-i) and (B-i): equally distributed (E.D.) power and optimized current distribution between coils. Conserved power using the optimal approach is equal to the area between the two curves. (A-ii) and (B-ii) show the current distribution using both actuation schemes. (A-iii) and (B-iii) show total power conserved using the power-optimized controller. The current distribution optimization minimizes power consumption and Joule heating effects by prioritizing the axial coils 6 when achieving angles between 90° and 160° (FIG. 8A-ii), resulting in an increase in the conserved power. Beyond 160°, the side coils 7-10 generate more torque resulting in current reprioritization and thus a loss in the conserved power. This phenomenon is also observed when $\gamma=90°$ (FIG. 8B-ii); between 20° and 50°, the axial coils 6 are prioritized. Angles less than 20° cause current redistribution toward the side coils 7-10 as the catheter aligns parallel to the B$_0$ field vector. Due to the differences in coil resistance between the saddle/side and axial coils 6, 7-10, significant power changes can be observed (FIG. 8A-iii, B-iii). FIG. 8A-iii demonstrates 3 mW of conserved power for smaller angles and as much as 50 mW for larger angles when the catheter 1 begins aligned with the B$_0$ field vector. FIG. 8B-iii indicates a conserved power magnitude of 10 mW when $\gamma=90°$ and the catheter 1 aligns parallel to the B$_0$ field vector. 25% conserved power regardless of initial orientation may be demonstrated. Such power conservation improves overall catheter safety during steering at low rotation angles, and increases the catheter workspace up to 10° at higher angles. The above given description applies mutatis mutandis to the endoscope 15.

In a third step S3 of the method the determined minimum current (I_side1, I_side2, I_axial) is supplied to each coil of the set of coils 6, 7-10, respectively, such that the tip 2, 16 of the medical device 2, 15 carries out the movement.

The third step S3 may comprise, in case the medical device is the endoscope 15, actuating the end effector 21 thereof by supplying a current to the further set of coils 22. In case the end effector 21 comprises the grasper, actuating the end effector 21 may comprise opening and/or closing the jaws 23 of the grasper 21 by applying the current to the further set of coils 22. The opening may be a movement where the jaws of the grasper are moved away from each other by turning them around the pivot joint 24 and the closing may be a movement where the jaws 23 of the grasper are moved towards each other by turning them around the pivot joint 24. The method may comprise ablating and/or killing tissue, optionally comprising tumor cells, such as cancerous brain tumor cells, using the Joule heating caused by the current supplied to the further set of coils 22 for actuating the end effector 21, optionally for opening and closing the jaws 23 of the grasper.

The Joule heating caused by actuating the grasper may be used in the third step S3 of the method for cauterization. More specifically, the cauterization comprises actuating the end effector by applying a current to the further set of coils 22, and ablating and/or killing tissue, optionally comprising tumor cells, using the Joule heating caused by the current supplied to the set of coils for actuating the end effector.

This will be explained in detail below with respect to one specific implementation of the disclosure which is described solely for explanatory purposes and is not intended to limit the scope of the disclosure, especially the claims, in any way.

With the proposed design of the MM-driven endoscope 15 described above, leveraging the high (3-7 T), external magnetic field of an MR scanner for heat-mitigated steering within the ventricular system of the brain becomes possible. The Lorentz force-based grasper may be used for diseased tissue manipulation and ablation, i.e., cauterization. Feasibility studies show the neuroendoscope 15 can be steered precisely within the lateral ventricle to locate a tumor using both MRI and endoscopic guidance. Results also indicate grasping forces as high as 31 mN are possible and power inputs as low as 0.69 mW can cause cancerous tissue ablation.

Figure 9:
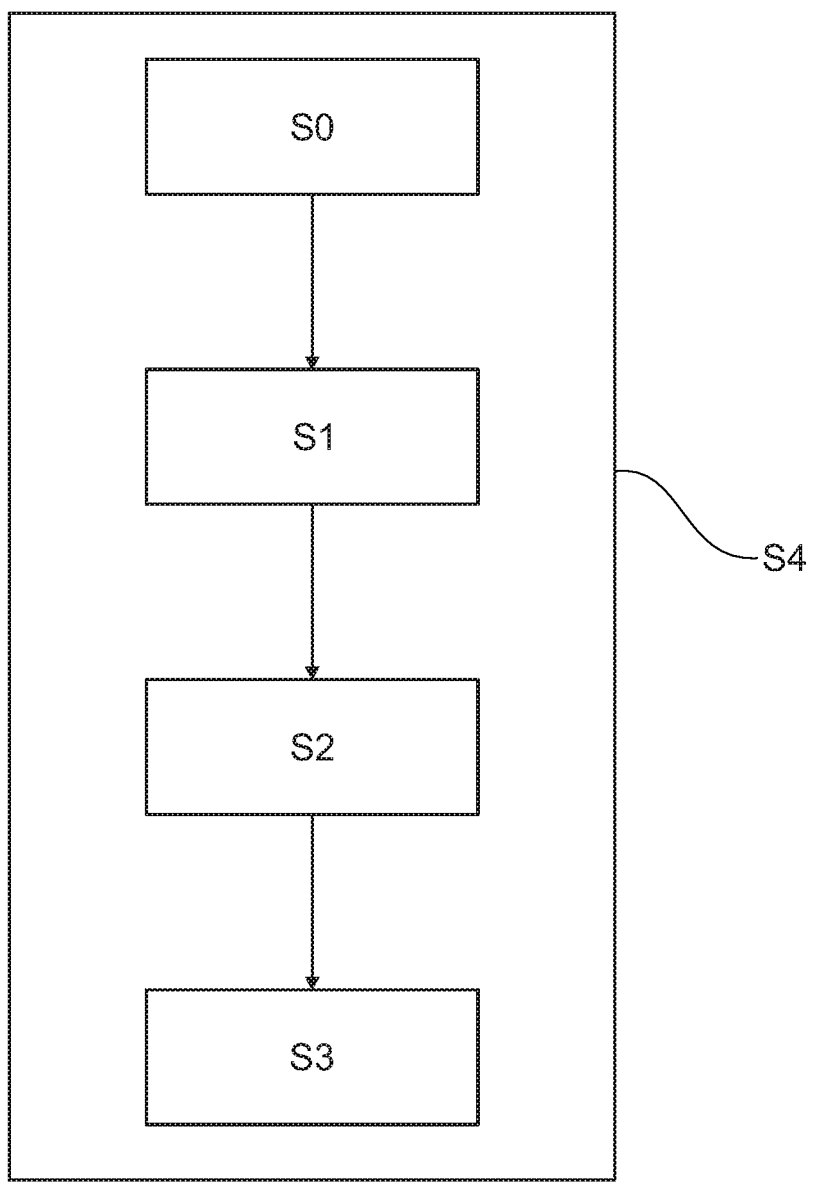
FIG. 9 shows a flow diagram of a further method for controlling a movement of a medical device in a magnetic field.

In FIG. 9 a flowchart for a flow diagram of a further method for controlling the movement of the medical device 1, 15 in a static magnetic field produced by a medical imaging device, here a magnetic resonance imaging device. The method comprises the above described steps S1-S3. The method further comprises in an initial step S0 receiving user input with respect to the movement via a user interface, optionally comprising a joystick. The user interface may be connected to the medical device 1, 15. The method further comprises a fourth step S4 carried out simultaneously to the steps S0-S4, wherein this step S4 comprises determining an actual position of the medical device 1, 15, optionally the tip 2, 16 thereof, using medical imaging, here the MRI, continuously and displaying the determined position of the medical device continuously on a display device with respect to a tissue, optionally of a human being or an animal, in which the medical device 1, 15 is located. The display device may be connected to the medical imaging device.

What is claimed is:
1. A method for controlling a movement of a medical device in a magnetic field, the medical device comprising a set of coils, wherein the method comprises:
determining a torque that needs to be applied onto the medical device such that the medical device carries out the movement, determining a minimum current that needs to be supplied to each coil of the set of coils, respectively, to reach the determined torque by solving an optimization problem, and supplying the determined minimum current to each coil of the set of coils, respectively, such that the medical device carries out the movement wherein the optimization problem is defined as follows:

$$I^* = \underset{I}{\arg\min} \|\tau_{coils} - \tau_{des}\|^2 + \alpha \|I\|_R^2$$

wherein:

I represents a current supplied to each coil of the set of coils, respectively, $\tau_{coils}$ represents a total torque generated by the set of coils when being supplied with the current I, $\tau_{des}$ represents the torque that needs to be applied onto the medical device such that the medical device carries out the movement, and R represents a resistance of each coil of the set of coils α represents a constant determined using a grid search to find a best fitting.

2. The method according to claim 1, wherein determining the torque comprises solving a further optimization problem to minimize the torque to be applied onto the medical device such that the medical device carries out the movement.

3. The method according to claim 1, wherein the medical device comprises a flexible, substantially rod shaped portion and the movement comprises a deformation of said rod shaped portion resulting in a movement of a tip of said rod shaped portion.

4. The method according to claim 3, wherein solving the further optimization problem comprises:

determining the deformation of said rod shaped portion that is needed for the movement of the tip of said rod shaped portion from an actual location to a desired location such that a torque that is required for the deformation of said rod shaped portion is minimized, and determining the torque that needs to be applied onto the medical device such that the medical device carries out the movement to be equal to the torque that is required for the deformation of said rod shaped portion.

5. The method according to claim 4, wherein the deformation that is needed for the movement of the tip of said rod shaped portion from the actual location to the desired location is determined using a model.

6. The method according to claim 1, wherein the method comprises receiving user input with respect to the movement via a user interface.

7. The method according to claim 1, wherein the method comprises:

determining an actual position of the medical device using medical imaging, and automated controlling of the movement based on the determined actual position.

8. The method according to claim 1, wherein the method comprises displaying, on a display device connected to the medical device, an actual position of the medical device and/or a position of the medical device after carrying out the movement.

9. The method according to claim 8, wherein the method comprises displaying the actual position of the medical device and/or the position of the medical device after carrying out the movement with respect to a tissue.

10. The method according to claim 1, wherein the magnetic field is produced by a medical imaging device.

11. The method according to claim 1, wherein the magnetic field is a static magnetic field.

12. The method according to claim 1, wherein the medical device comprises a catheter.

13. The method according to claim 12, wherein the catheter comprises:

a tip, the set of coils surrounding the tip, and power wires arranged to supply the set of coils with electrical energy.

14. The method according to claim 13, wherein the set of coils comprises four side coils arranged around the tip such that a straight line standing orthogonal on a longitudinal direction of the tip crosses a center of the respective side coil.

15. The method according to claim 14, wherein:

a first and a second one of the side coils are connected in series, a third and a fourth one of the side coils are connected in series, the first and the second one of the side coils are arranged on opposite sides of the tip, and the third and the fourth one of the side coils are arranged on opposite sides of the tip and in-between the first and the second one of the side coils.

16. The method according to claim 14, wherein the four side coils are arranged on the same circuit board.

17. The method according to claim 12, wherein a turn number of at least one of the four side coils is between 2 and 40.

18. The method according to a claim 12, wherein the set of coils comprises at least one axial coil arranged around the tip such that a straight line extending in parallel to the longitudinal direction of the tip crosses a center of the at least one axial coil.

19. The method according to claim 12, wherein at least one of the coils of the set of coils was manufactured using laser machining, laser lithography and/or manually wound.

20. The method according to a claim 12, wherein at least one of the coils of the set of coils has an Archimedean spiral coil design.

21. The method according to claim 12, wherein at least one of the coils of the set of coils has an in-plane design.

22. The method according to claim 1, wherein the medical device comprises an endoscope.

23. The method according to claim 22, wherein the endoscope comprises:

a tip, the set of coils surrounding the tip, and power wires arranged to supply the set of coils with electrical energy.

24. The method according to claim 23, wherein the set of coils comprises four side coils arranged around the tip such that a straight line standing orthogonal on a longitudinal direction of the tip crosses a center of the respective side coil.

25. The method according to claim 24, wherein:

a first and a second one of the side coils are connect in series, a third and a fourth one of the side coils are connect in series, the first and the second one of the side coils are arranged on opposite sides of the tip, and the third and the fourth one of the side coils are arranged on opposite sides of the tip and in-between the first and the second one of the side coils.

26. The method according to claim 24, wherein the four side coils are arranged on the same circuit board.

27. The method according to claim 23, wherein the endoscope comprises an end effector connected to the tip of the endoscope.

28. The method according to claim 27, wherein the end effector comprises a further set of coils for actuating the end effector.

29. The method according to claim 28, wherein the method comprises actuating the end effector by applying a current to the further set of coils.

30. The method according to claim 29, wherein the method comprises ablating and/or killing tissue using the Joule heating caused by the current supplied to the further set of coils for actuating the end effector.

31. The method according to claim 28, wherein:

the end effector comprises a grasper with two jaws connected pivotally to each other, and the further set of coils comprises at least one side coil arranged at each one of the two jaws, respectively.

32. The method according to claim 31, wherein actuating the end effector comprises opening and/or closing the jaws of the grasper by applying the current to the further set of coils.

33. The method according to claim 22, wherein a turn number of at least one of the four side coils is between 2 and 40.

34. The method according to claim 22, wherein the set of coils comprises at least one axial coil arranged around the tip such that a straight line extending in parallel to the longitudinal direction of the tip crosses a center of the at least one axial coil.

35. The method according to claim 22, wherein at least one of the coils of the set of coils was manufactured using laser machining, laser lithography and/or manually wound.

36. The method according to claim 22, wherein at least one of the coils of the set of coils has an Archimedean spiral coil design.

37. The method according to claim 22, wherein at least one of the coils of the set of coils has an in-plane design.

38. The method according to claim 22, wherein the tip of the endoscope comprises:

a camera, an illumination device, and/or an opening of an irrigation channel extending through the endoscope.

* * * * *